United States Patent [19]

Scott

[11] Patent Number: 4,765,907
[45] Date of Patent: Aug. 23, 1988

[54] WEARABLE, CONTINUOUSLY INTERNALLY OPERABLE AND EXTERNALLY REGENERABLE DIALYSIS DEVICE

[75] Inventor: Robert D. Scott, West Covina, Calif.

[73] Assignee: Research Development Systems, Inc., Pasadena, Calif.

[21] Appl. No.: 662,250

[22] Filed: Oct. 18, 1984

Related U.S. Application Data

[63] Continuation-in-part of Ser. No. 594,203, Mar. 28, 1984, abandoned.

[51] Int. Cl.$^4$ ............................................. B01D 13/00
[52] U.S. Cl. .................................. 210/648; 210/321.78
[58] Field of Search .................... 210/648, 321.3, 321.4, 210/321.2, 321.78; 604/27, 28, 29; 128/DIG. 3

[56] References Cited

U.S. PATENT DOCUMENTS 3,388,803  6/1968  Scott ................................ 210/321.3
3,505,686  4/1970  Bodell ........................... 40/321.4 X
4,081,372  3/1978  Lyman Atkin et al. ..... 210/321.2 X
4,148,497  1/1980  Kolff et al. ............................ 604/27
4,276,175  6/1981  Bower .............................. 210/648 X
4,338,190  7/1982  Kraus et al. ...................... 604/29 X

OTHER PUBLICATIONS

Bodell, et al., "An Implantable Artificial Lung", from JAMA, 1-25-65, vol. 191, #4, pp. 125-127, copy.

Primary Examiner—Frank Spear
Attorney, Agent, or Firm—Louis J. Bachand

[57] ABSTRACT

Wearable, continuously internally operable, externally regenerable dialysis system in which body fluids are dialyzed against a first dialysis fluid within a chamber in the body without invasion of veins or arteries, the chamber being a body cavity or a semi-permeable wall within the body, the dialysis fluid being regenerated in a chamber outside the body against a second dialysis fluid which is continuously regenerated in a belt supported apparatus, the internal and external chambers being in fluid communication.

53 Claims, 4 Drawing Sheets

WEARABLE, CONTINUOUSLY INTERNALLY OPERABLE AND EXTERNALLY REGENERABLE DIALYSIS DEVICE

REFERENCE TO RELATED APPLICATION

This application is a continuation-in-part of my earlier filed and copending application, Ser. No. 06/594,203 filed Mar. 28, 1984, now abandoned, the disclosure and claims of which are hereby incorporated by this reference.

TECHNICAL FIELD

This invention has to do with kidney dialysis and more particularly with novel apparatus and methods for effecting artificial kidney dialysis. The invention is specifically concerned with continuously effected dialysis within the body against body fluids outside of veins and arteries, e.g. such fluids as circulate among and lubricate the organs of the body, particularly fluids in the region of the large and small intestine behind the peritoneum. In a particularly preferred form the invention utilizes the blood-rich rectum as a dialysis locus for dialysis without invasion of veins or arteries and within the body without withdrawl of blood. The apparatus is wearable, dialyzes continuously and is self regenerating to make the user more independent than has heretofore been possible.

BACKGROUND

It is conventional to withdraw blood from the body, pass it in dialyzing contact with a purging liquid contained within an artificial kidney machine, herein referred to as an "in vitro" device, so as to withdraw from the blood waste or contaminants normally removed by a person's kidneys, where the normal kidney function s missing or insufficient. Such practice while common is beset with many disadvantages, not the least of which is the need to chemically condition the blood against unwanted clotting response to the dialyzing treatment. Other disadvantages include periodic chemical imbalance in the user's body as the usual kidney dialysis treatment is given but several times a week resulting in a far from natural cycling between unduly waste-laden and ultra-clean conditions responsive to the schedule of treatments.

In my earlier patents, U.S. Pat. Nos. 3,388,803 and 3,884,808, I disclosed externally wearable artificial kidney devices through which blood was circulated as the user moved through his daily routine, the dialzing fluid being regenerated by a system of filters and make-up solids continuously fed to the dialysis fluid. As superior as these devices were to stationary "dialysis center" type dialysis devices, the problems inherent in techniques involving blood circulation outside the body remained.

DESCRIPTION OF THE INVENTION

It is therefore among the objects of the invention to provide a novel dialysis system for humans, and more particularly to provide such a system in which the dialyzing effectiveness of earlier systems is retained, but in which in addition the problems inherent in dialyzing blood outside the body are avoided. Another object is to continuously conduct dialysis and within the body, herein referred to as "in vivo", or "internally operable" dialysis, and to regenerate the dialyzing fluid outside the body so that the dialyzing fluid and not blood circulates to and from the body. It is a further object to use blood or nonblood body fluids for purposes of dialysis against a first dialyzing fluid, and to collect contaiminants from such fluids in noncritical areas of the body, such as adjacent the intestines, in the rectum, or within the peritoneal cavity, pass the waste products in the dialysis fluid from the body, regenerate the dialysis fluid, against a second dialysis fluid which is continuously regenerated by filtration and make-up solids as necessary to have the composition needed to adjust the composition of the first dialysis fluid, dispose of the waste products to the second dialysis fluid, under the pressure of a pump means which can be conveniently integrated with the system; the entire assemblage being carryable on the body as a waist-encircling belt. In particular embodiments, the dialysis zone or chamber comprises a semipermeable membrane, either artificial such as Cupraphane or the like, or natural, such as a section of the uers's own tissue, e.g. a vein taken from the person's leg, or preferably a section of the intestine which is removed and reconnected so as to be common living tissue with the intestine but to be out of fluid communication with the waste products within the intestine.

The foregoing objects and other objects of the invention to become apparent hereinafter are realized with a wearable, continuously internally operable and externally regenerable dialysis device comprising means concurrently dialyzing a confined dialysis fluid against body fluids within the body and regenerating the dialysis fluid outside the body, which means typically includes pump means for exchanging the dialysis fluid from within and outside the body, an internal chamber disposed within the body for confining the dialysis fluid, the chamber having a semipermeable wall adapted to dialysis, an external chamber disposed outside the body, the external chamber having a semipermeable wall for dialyzing spent dialysis fluid therein against a regenerating fluid, and conduit means continuously communicating the confined portion of the dialysis fluid with dialysis fluid outside the body.

More particularly, there is provided in accordance with the invention, in one embodiment a wearable, continuously internally operable and externally regenerable dialysis device comprising means concurrently dialyzing a confined dialysis fluid against body fluids within the body and regenerating the dialysis fluid outside the body, which means typically includes pump means for exchanging the dialysis fluid from within and outside the body, an internal chamber disposed within the body for confining the dialysis fluid, the chamber having a semipermeable wall adapted to dialysis, an external chamber disposed outside the body, the external chamber having a semipermeable wall for dialyzing spent dialysis fluid therein against a regenerating fluid, and conduit means continuously communicating the confined portion of the dialysis fluid with dialysis fluid outside the body.

More particularly, there is provided in accordance with the invention, in one embodiment a wearable, continuously internally operable and externally regenerable dialysis device comprising internal chamber means disposed within the body for confining a common dialyzing fluid in body fluid dialyzing relation, external chamber means outside the body in open communication with the internal chamber means and having a semipermeable wall for regenerating dialysis of common dialysis fluid therein against a second dialysis fluid, and pump means for exchanging regenerated dialysis fluid with internal chamber-confined dialysis fluid.

In this and like embodiments the invention contemplates apparatus wherein the internal chamber means comprises a semipermeable wall adapted to dialysis of body fluids against dialysis fluid confined within the internal chamber; the internal chamber means comprises a section of the intestine out of interior fluid communication with the intestine but constituted of common living tissue therewith which may further include also a semipermeable wall structure within the intestine section defined internal chamber in body fluid dialyzing relation.

Or, the internal chamber means comprises a waste-products by-passed section of the rectum. In certain embodiments of this form of the invention, the invention further typically employs a semipermeable wall structure within the rectum section in body fluid dialyzing relation. As in other embodiments the device also includes conduit means for removal of spent dialysis fluid extending between the internal chamber and the external chamber, e.g. via the anus.

The wearable, continuously internally operable and externally regenerable dialysis device preferable includes also second dialysis fluid means comprising a supply of fluid adapted to regenerate the first dialysis fluid, and the external chamber semipermeable wall having extended disposition within the second dialysis fluid supply for dialysis of the first dialysis fluid and removal of excess water and/or salts therefrom; means to separate excess water and/or salts from the second dialysis fluid to disposal; and means to mount the external chamber on the body, the mounting means including belt means adapted to support the device.

In a particularly preferred embodiment the invention provides a wearable, continuously internally operable and externally regenerable, dialysis device in which the external chamber is an elongated tube, an envelope containing the second dialysis fluid supply is provided surrounding the tube, as well as a water supply for separation of excess water from the first dialysis fluid in advance of dialysis against the second dialysis fluid supply in the envelope.

Typically in the foregoing embodiments, the regenerating means is fluid exchange-responsive, the means to exchange the first dialysis fluid includes a first pump in open communication with the internal and external chambers, there is a second pump, and an envelope surrounding the external chamber and containing a supply of second dialysis fluid make-up solids in flow communication with the second dialysis fluid for adding such solids to the second dialysis fluid during pumping thereof by the second pump, and suitably filter means in flow communication with the envelope for separating filterable components from the second dialysis fluid during pumping thereof by the second pump, and suitably filter means in flow communication with the envelope for separating filterable components from the second dialysis fluid, including such components dialyzed into the second dialysis fluid from the first dialysis fluid.

In a more specific form, the invention comprises a wearable, continuously internally operable and externally regenerable, dialysis device comprising a body fluid-dialyzing semipermeable generally tubular internal chamber resistant to deterioration from exposure within the body, and an external chamber, the internal chamber being adapted to extended disposition within a user's body in body fluid-dialyzing relation and freely of interior communication with veins and arteries, the external chamber being in continuous open communication with the internal chamber, a pump to exchange a first dialysis fluid between the internal chamber and the external chamber, and means to regenerate the first dialysis fluid during a passage through the external chamber for return to the internal chamber. In this form, the internal chamber is elongated and located inward of the peritoneum, and includes also a continued extent of the chamber defining a conduit for passing first dialysis fluid through the peritoneum; or the internal chamber compises a section of the large or small intestine out of interior fluid communication with the intestine from which it is taken, but constituted of common living tissue therewith; and the external chamber is an elongated tube adapted to contain the first dialysis fluid, and there is included also an envelope surrounding the tube for holding the second dialysis fluid against the tube in dialyzing relation to regenerate the first dialyzing fluid, e.g. the envelope comprises a second tube surrounding the external chamber tube along its length.

There is further provided valve means selectively openable to draw the second dialysis fluid from the envelope.

In typical embodiments of the wearable, continuously internally operable and externally regenerable, dialysis device according to the invention, the means to exchange the first dialysis fluid includes a first pump in open communication with the internal and external chambers, and the device further includes means to regenerate the first dialysis fluid by addition or subtraction of components for dialysis in the first dialysis fluid; a waist encircling belt carrying the envelope and supporting the first pump and regenerating means at the hip region of the wearer; the external chamber is disposed within the belt in multiply reverse-turned relation, and a second pump for circulating the second dialysis fluid through the envelope is provided.

In a still further embodiment the invention contemplates provision of a wearable, continuously internally operable and externally regenerable, dialysis device comprising a body fluid dialyzing internal chamber sized and arranged to define an extended dialyzing interface with body fluids outside the veins and arteries of the user's body, the internal chamber being integral with living tissue of the user's intestine, or rectum, and free of interior open communication with the intestine.

More preferably there is provided a wearable, continuously internally operable and externally regenerable, dialysis device comprising a body fluid dialyzing internal chamber sized and arranged to define an extended dialyzing interface with body fluids outside the veins and arteries of the user's body, the internal chamber being defined by a closed semipermeable wall disposed within the user's rectum free of interior open communication with the user's intestine.

In each of these just noted embodiments the device further typically includes means to exchange the first dialysis fluid from within the body into and through the external chamber for regeneration against a second dialysis fluid of different composition for adding or subtracting components from the circulating dialysis fluid according to the user's need.

The rectum utilizing embodiment may thus be defined as a wearable, continuously internally operable and externally regenerable,dialysis device comprising a body fluid-dialyzing internal chamber and an external chamber in continuous open communication therweith, the internal chamber being defined at least in part by the rectum out of communication with the intestine and adapted to contain dialyzing fluid in body fluid-dialyzing relation, pump means to exchange a first dialysis fluid between the internal and external chambers and means to dialyze the first dialysis fluid in the external chamber for return for the internal portion and concurrently with the exchange; wherein typically the external chamber is an elongated tube, there is an envelope surrounding the tube, and a second dialyzing fluid within the envelope for regenerating the circulating dialysis fluid within the external chamber, a valve-controlled means to tap the second dialysis fluid from the envelope, and the means to exchange the first dialysis fluid includes a first pump in open communication with the chambers, There is further provided a second pump in open communication with the envelope, a solids adjustment zone in open communication with envelope comprising means selected from a filter means and a supply of second dialysis fluid make-up solids in flow communication with the zone for adding to or removing solids from the second dialysis fluid pumped by the pump. Typically, the first and second pumps are external of the body.

In yet another embodiment there is provided a wearable, continuously internally operable and externally regenerable, dialysis device for a person having a by-passed rectum as by a colostomy, the device having an internal chamber and an external chamber, the internal chamber being defined by the rectum of the wearer, whereby fluids passed from the device into the rectum pass in fluid-dialyzing relation with the rectum interior wall, the external chamber comprising a body fluid-dialyzing semipermeable chamber in open communication with the internal and external chambers, and means to regenerate the first dialysis fluid within the external chamber for return to the internal chamber for continuing body fluid dialysis. Such embodiment further contemplates use of a deflector adapted to deflect dialysis fluid within the rectum into dialyzing proximity with the rectum interior wall, and/or use of a closed semipermeable wall disposed within the rectum, and the means to exchange dialysis fluid further including means defining a first fluid passage to the rectum, and means defining a second fluid passage out of the rectum via the anus.

As previous embodiments, typically the external chamber is an elongated tube adapted to contain the first dialysis fluid, an envelope surround the tube for holding the second dialysis fluid against the tube in dialyzing relation to regenerate the first dialyzing fluid; the envelope comprises a second tube surrounding the external chamber tube along its length; valve means are provided selectively openable to draw an aliquot portion of the second dialysis fluid from the envelope, the means to exchange the first dialysis fluid includes a first pump in open communication with the chambers, means are provided to regenerate the second dialysis fluid by addition or subtraction of components for dialysis of the first dialysis fluid, the pump and regenerating means are body-external, a waist encircling belt is provided carrying the envelope and supporting the pump and regenerating means at the hip region of the wearer, the body-external portion being disposed within the belt in multiply reverse-turned relation.

The invention further contemplates method for the continuous dialyzing of body fluid within the body, including urging a first dialysis fluid through the body in body-fluid dialyzing relation, dialyzing the first dialysis fluid against a second dialysis fluid differing in composition from the first dialysis fluid in first dialyzing fluid regenerating relation. The method further contemplates defining an internal zone within and an external zone without the user's body freely of interior communication with veins and arteries of the body for exchange of the first dialysis fluid between the zones, the external zone comprising a semipermeable membrane, the internal zone being in dialyzing communication with body fluids within the body, and the external zone being in dialyzing communication with the second dialysis fluid outside the body; employing a tissue of the user's body to define the internal zone in dialyzing communication with body fluids; selecting a section of the user's intestine and connecting the section to be common living tissue with the intestine but out of interior fluid communication therewith to define the internal zone in dialyzing communication with body fluids; or selecting a section of the user's rectum isolated from the intestine to define the internal zone, introducing the first dialyzing fluid thereinto and withdrawing the fluid at the anal opening, the fluid being diffused in dialyzing contact with the rectum wall between its introduction and withdrawl; and interposing a semipermeable wall between the first dialysis fluid and the rectum wall, whereby the semipermeable wall dialyzes body fluids within the rectum wall against the first dialysis fluid.

In another embodiment there is provided in accordance with the invention the method for continuous dialysis including concurrently dialyzing a confined dialysis fluid against body fluids within the body and concurrently regenerating the dialysis fluid outside the body. In such embodiment the invention contemplates: exchanging the dialysis fluid outside the body for dialysis fluid within the body to renew the dialysis fluid within the body; employing a section of the user's body tissue to confine the dialysis fluid within the body; employing a semipermeable membrane to confine the dialysis fluid within the body; dialyzing spent dialysis fluid from within the body against a regenerating fluid outside the body; continuously exchanging the confined portion of the dialysis fluid with the dialysis fluid outside the body; internally dialyzing the body while externally regenerating the dialysis fluid including confining within the body a common dialyzing fluid in body fluid dialyzing relation, regenerating the common dialysis fluid against a second dialysis fluid outside the body, and exchanging the regenerated dialysis fluid with the confined dialysis fluid; confining the common dialysis fluid within living tissue of the user; confining the common dialysis fluid within a semipermeable membrane; and dialyzing the semipermeable membrane confined fluid against the rectum wall of the user.

THE DRAWING

The invention will be further described as to an illustrative embodiment in connection with the attached drawings in which.

PREFERRED MODES

The disclosures of my earlier patents, U.S. Pat. Nos. 3,388,803 and 3,884,808 are hereby incorporated herein by reference, including the typical composition of dialysis fluids therein set forth.

Figures 1, 2, 3, 4:
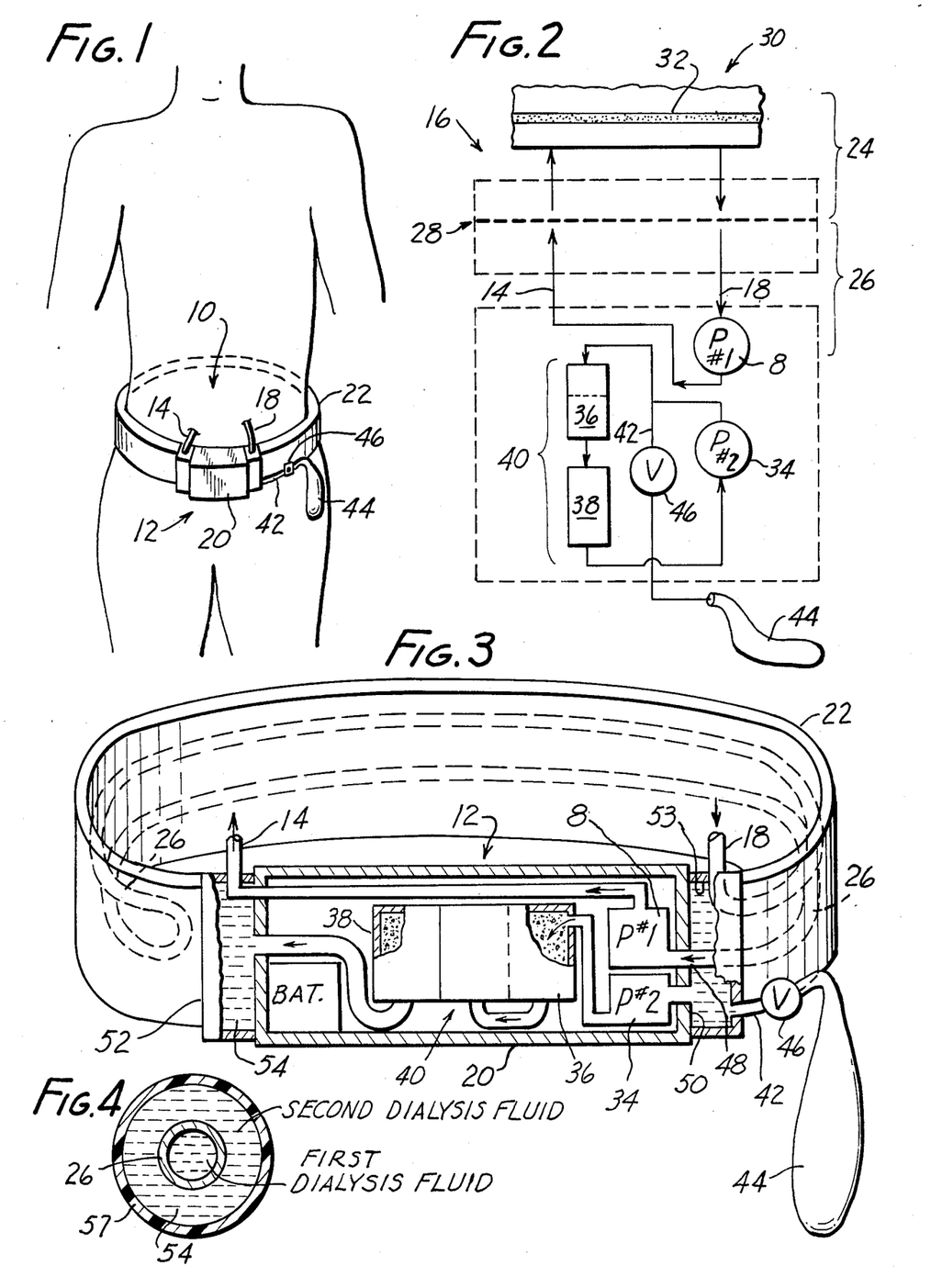
FIG. 1 is a pictorial view of the device of the invention as worn by a user.
FIG. 2 is a schematic view of the dialysis system body-internal and body-external chambers showing their functional relationship.
FIG. 3 is a generally sectional view of the external parts of the dialysis device, shown attached to the supporting belt.
FIG. 4 is a sectional view of an alternative embodiment.

In FIG. 1, the dialysis device of the invention is shown at 10 and comprises means 12 to circulate continuously into and out of the body a first dialyzing fluid of a selected composition typically to withdraw contaminants from the body fluids, but optionally to add e.g. medicaments to the body. "Continuously operable" in the present specification and claims refers to the capacity of the present apparatus and method for effecting dialysis on an ongoing basis analogous to the body processes they replace whereby dialysis is essentially constant, but on an asneeded basis, with pauses if desired to match the body's needs from time to time and as close as possible to steady-state operation for optimum imitation of the natural kidney function, but not necessarily always in operation or at the same rate. Addition or withdrawl is effected by osmotic diffusion through the semipermeable membrane to be described. A typical usage of the first dialysis fluid is the withdrawl of body fluid components such as uric acid which circulate in the blooddstream and perfuse into the body fluids at the exterior surface of veins, arteries and other body parts, such as organs, including the intestine and the rectum, and from which they can be removed in accordance with the present invention.

The circulating means 12 includes a first pump 8, an inlet 14 to the body from the external dialysis fluid chamber 16 (FIGS. 2 and 3) for return of regenerated first dialysis fluid to the body for further dialysis, and an outlet 18 from the body to the external dialysis fluid chamber. To achieve regeneration of the first dialysis fluid, a second dialysis fluid is provided, kept entirely outside the body and against which the first dialysis fluid is dialyzed. This second dialysis fluid is typically of a composition like the first, but varied to add to or subtract from the first dialysis fluid those materials needed for effective functioning of the first dialysis fluid within the body, e.g. to effect the kidney function.

The specific composition of either the first or second dialysis fluid is not a part of this invention since such compositions are well known and commercially available, and herein need only be able to dialyze body fluids in the case of the first dialysis fluid in imitation of the normal kidney function (a process for which typical fluids are well known), or, in the case of the second, wholly external dialysis fluid, to dialyze the first dialysis fluid so as to regenerate that fluid for further imitation of the normal kidney function. For purposes of regenerating the second dialysis fluid, and indirectly the first dialysis fluid, the device includes a second pump 34 for second dialysis fluid pumping and a solids adjustment zone 40 for filtration (which includes surface adsorption herein) in filter tank 36, all located within housing 20; an extended dialysis path distributed within and supported by belt 22, and a tap 24 for draining the second dialysis fluid and all carried on the hips of the wearer as shown, with the housing 20 functioning as a belt buckle.

It is noteworthy that with the present system of dialysis, which provides for constant removal of water from the dialysate through tap 24, under pressure response if desired, the undue accumulation of water in the system is avoided, freeing the user to drink water or take in quantities of liquid which have been heretofore proscribed, auguring a new level of convenience and comfort for artificial kidney users, and an increased sense of well being and independence.

In FIG. 2, the functional relationship of the device components is depicted. The first dialysis fluid containing chamber 16 is typically an elongated tubular member of semipermeable membrane material, including user body tissue as will be explained hereinafter. Dialysis fluid chamber 16 comprises a body-internal chamber 24 and a body-external chamber 26 divided for convenience of reference at skin line 28, but the chambers communicate with each other through the skin as shown, e.g. through suitable fittings such as stoma, not shown, ensuring sanitary connection. In the embodiments of FIGS. 7–11, the anus is used to pass fluid inlet and/or outlet tubes between the body-external and body-internal chambers, as will be hereinafter described.

Figure 7:
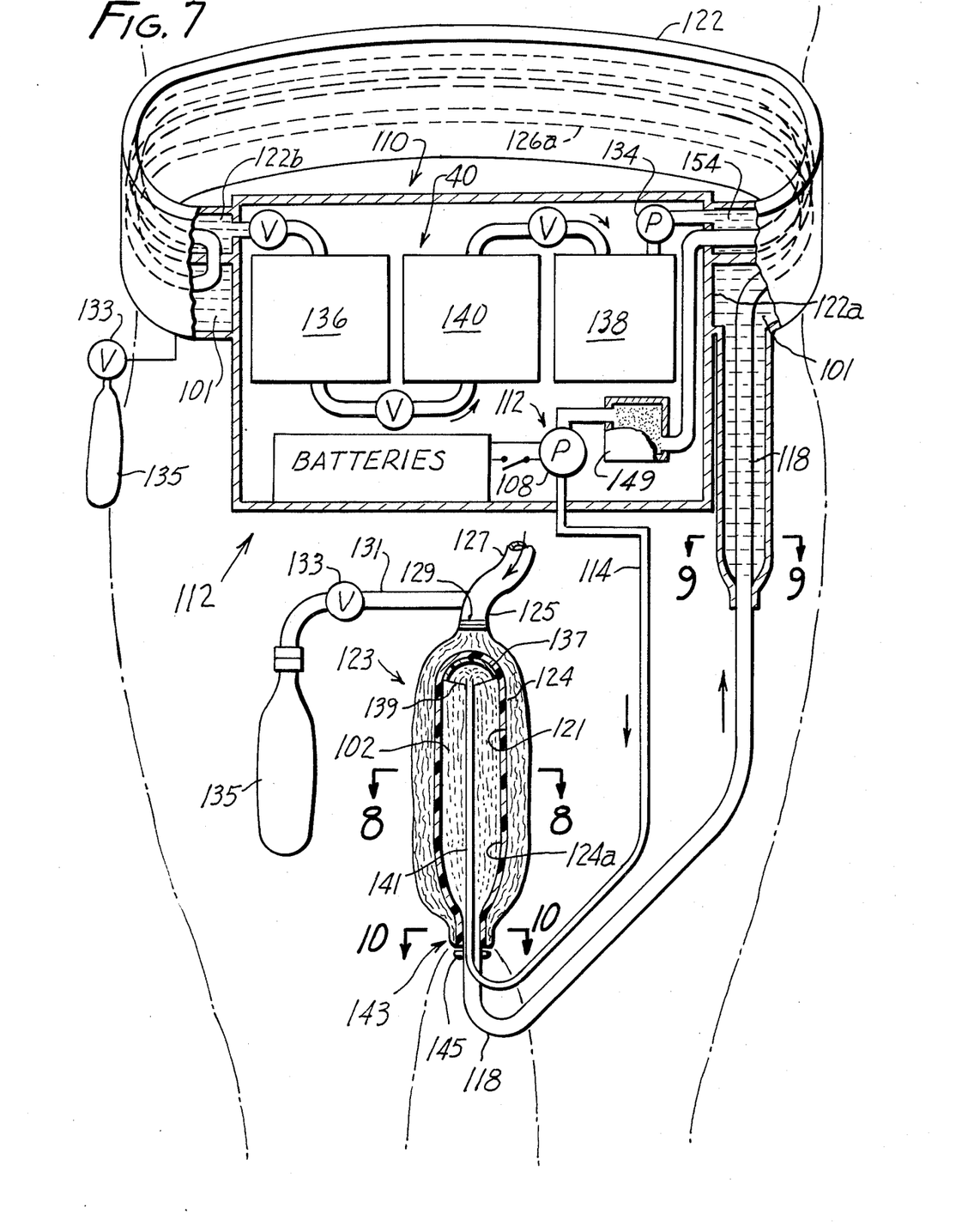
FIG. 7 is a diagrammatic view of the device having the body-internal chamber defined by a closed semipermeable wall interposed in the rectum.

The dialysis fluid is conveyed into the body through skin line 28 at inlet 14 from the external chamber 26 to the internal chamber 24, lying within body interior 30. Internal chamber 24, which may typically be a closed volume of tubular or bulbous configuration, cf. item 24 in FIG. 5 and item 124 in FIG. 7, is disposed suitably within the body for extensive dialyzing contact with body fluids but not directly in interior communication with intravenous or intraarterial blood, i.e. internal chamber 24 is free of invasion of or communication with the interior of all veins and arteries and in this embodiment typically lies within the body-interior 30 peritoneal cavity 30a adjacent the organs there, see FIG. 5 for example, particularly the large intestine, but such portion may lie anywhere within the body where it does not interfere with normal body functioning, is comfortable to the user, and is not crushed or bent so as to be blocked of fluid passage. See also FIG. 7. As presently contemplated for one embodiment, the abdominal cavity is ideal for location of the internal chamber by physical safety criteria, although better dialysis exchange is effected in other areas of the body as will be described hereinafter.

The internal chamber 24 conveys the first dialyzing fluid through the body cavity 30a in which it is disposed, and by well-know dialysis principles attracts through its semipermeable walls 32 water and salts within the surrounding body fluids including those perfusing the walls of veins and arteries, which would otherwise accumulate in the absence of effective kidney function, thereby purifying the body of such salts, and removing excess water as effectively as the blood dialysis contemplated in my earlier patents above referenced.

The dialysis fluid with its accumulated diffusants is conveyed from the body interior 30 to outside the body via outlet 18, under the pressure of battery-powered first pump 8, to regeneration by dialysis against the second dialysis fluid. As noted, the second dialysis fluid which is always outside the body, unlike the first dialysis fluid which circulates into and from the body, is repeatedly itself regenerated by removal of impurities by carbon absorption for example and addition of make-up solids such as salt and glucose at tanks 36, 38 respectively at zone 40, and is then returned to its own dialyzing function against the first dialysis fluid. For this purpose an envelope 53 is provided, defined by the belt 22, and arranged to ensure extended contact of the second dialysis fluid with the first dialysis fluid across the semipermeable membrane forming the external chamber 26.

The envelope 53 is periodically drained via tap 42 and collection vessel 44, controlled by valve 46.

With reference now to FIG. 3, an illustrative physical arrangement is depicted including belt 22 with a buckle 20 within which there is disposed the first pump 8 communicating on the intake side with the outlet 18 of the external chamber 26, the upstream portion of the chamber being multiply reverse-turned as shown within the belt 22 and disposed within the second dialysis fluid in envelope 53, whereby the upstream chamber fluid is purged of unwanted components or doped with medicaments or the like depending on the needs of the user and the composition of the second dialysis fluid relative to the first dialysis fluid.

As will be noted, in the embodiment of FIG. 3, the housing 12 in the form of buckle 20 defines the terminus of the external chamber 26 at 48 and plugs the belt 22 at both its open ends 50, 52 to define therewith envelope 53 for containing the second dialysis fluid 54 for regenerating the first dialysis fluid in external chamber 26 disposed in the second dialysis fluid 54.

Alternatively to the arrangement of external chamber 26 in second dialysis fluid 54 shown in FIG. 3, the entire belt need not be filled with second dialysis fluid, but a larger than chamber 26-diameter tubing may locally surround and enclose the chamber 26. In FIG. 4, chamber portion 26 is shown surrounded by envelope tube 57, which may be disposed in belt envelope 53 (shown in FIG. 3), whereby the second dialysis fluid 54 is confined about the chamber portion 26.

The second dialysis fluid 54 surrounding the external chamber 26 disposed in belt envelope 53 is circulated through a first double tank 36 in which absorbable impurities are removed by filtration by carbon for example, and then to a make-up solids tank 38 in which additives needed in the second dialysis fluid to maintain its appropriate composition for dialyzing the first dialysis fluid are added by metering solution of the solids in tank 38 effected by the passing of the second dialysis fluid thereover. The second dialysis fluid is returned to the envelope 53, for exchange with the first dialysis fluid in external chamber 26 which first fluid is then returned by the first pump 8 to the internal chamber 24 within the body interior 30 whereupon the cycle starts over.

It is highly advatageous in the present system that dialysis occurs continuously, whereby cyclical or periodic imbalances are avoided, and the user is free to do routine daily work without having to be at a central dialysis center coupled immovably to a machine.

Figure 5:
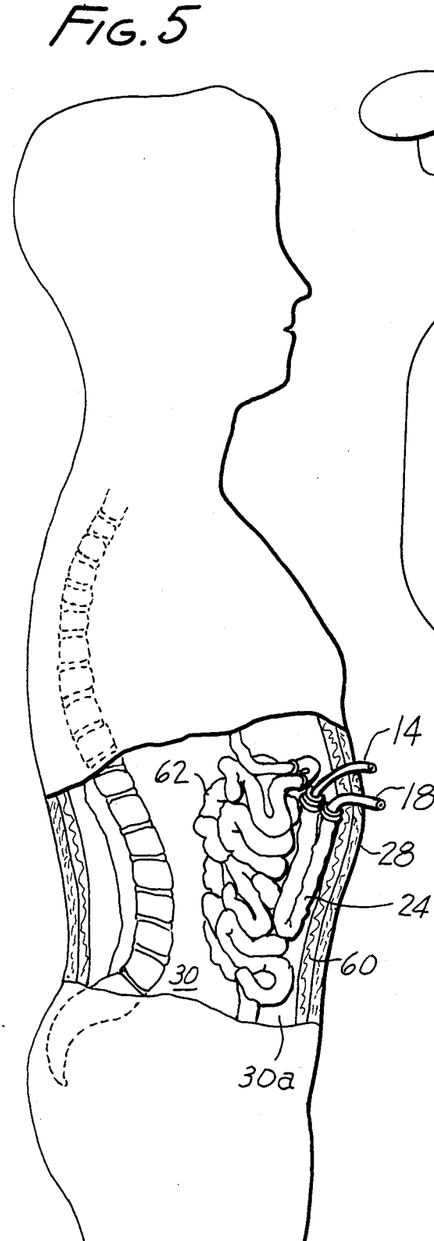
FIG. 5 is a side view, partly broken away to show the internal chamber of the device within the user's body.

With reference now to FIG. 5, the internal chamber 24 is shown disposed in zone 30, behind the peritoneum 60, and the skin line 28 and adjacent the large intestine 62, surrounded by body fluids which envelopes and lubricate the organs in the abdominal cavity enclosed by the peritoneum.

Figure 6:
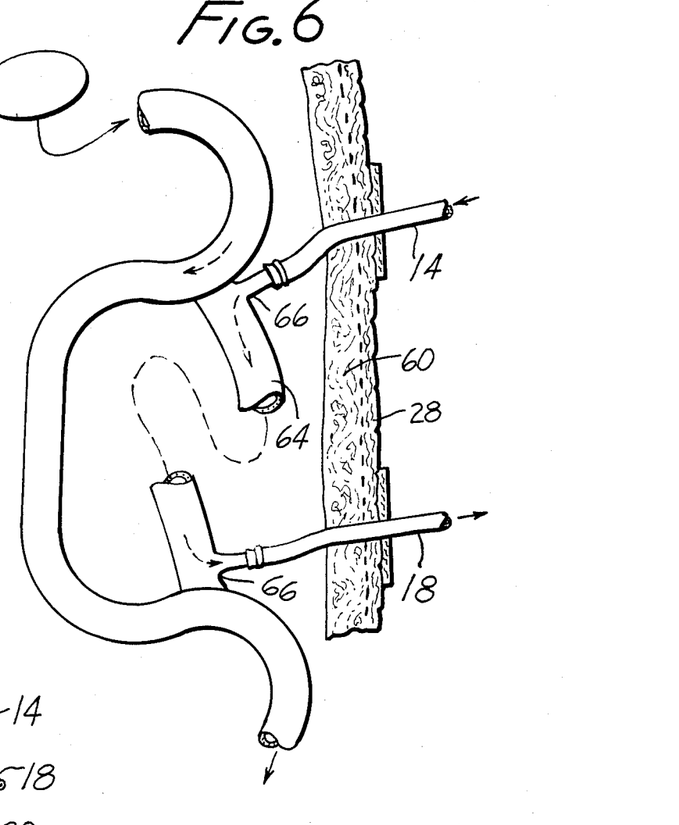
FIG. 6 is a view in elevation of the body-internal chamber depicted as common tissue with the large intestine, and connected for external regeneration.

In a further aspect of the invention, the internal chamber 24 may be comprised of living tissue, taken from a vein of the leg, or other suitable source within the user's body, and most preferably taken from the intestine itself. In this aspect of the invention, the arrangement is a depicted in FIG. 6. The large intestine 62 is cut to remove a section 64. The section 64 is sewn back onto the intestine 62 from which it was cut, but between opposed turns therein, as though defining a by-pass, but the section is not in fluid communication with the intestine interior as such would contaminate the dialysis fluid. Rather the exterior wall of the intestine 62 closes both ends of the section. The section 64 however as in a by-pass grows together with the intestine 62, forming common living tissue therewith, so that the section is continually self-renewing like all body tissue, free of rejection, and ideal for a perpetual dialysis function when communicated with the external regeneration system described above by means of T-fittings 66 or otherwise, enabling open communication with the external chamber 26 of the dialysis system.

With reference now to FIGS. 7-10, wherein like parts to the embodiments of FIGS. 1-8 are given like numbers plus 100, there is depicted a rectal installation of the internal dialysis chamber.

Figures 8, 9, 10, 11:
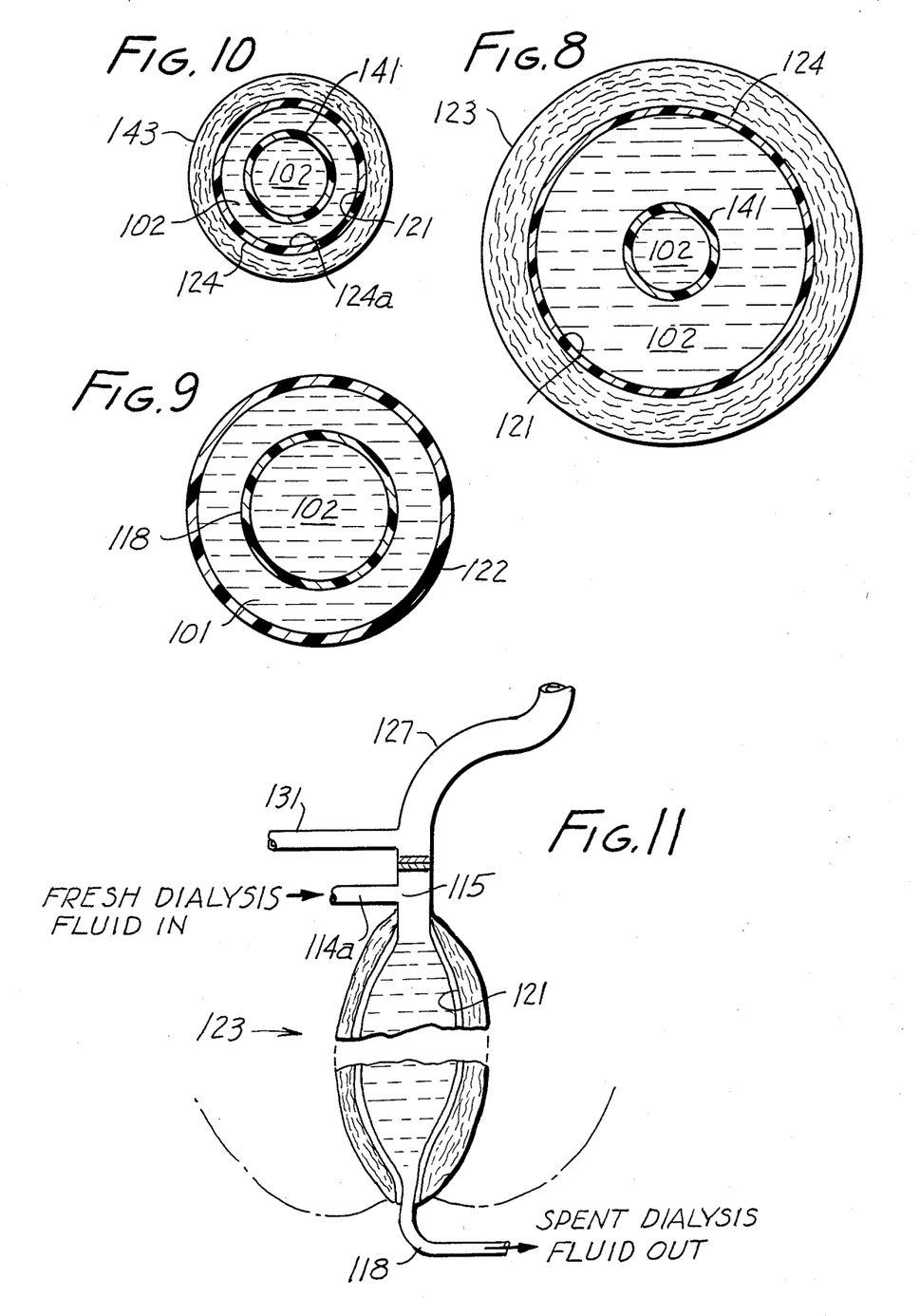
FIG. 8 is a view taken on line 8—8 in FIG. 7.
FIG. 9 is a view taken on line 9—9 in FIG. 7.
FIG. 10 is a view taken on line 10—10 in FIG. 7.
FIG. 11 is a fragmentary view like FIG. 7 showing the body-internal chamber defined by the wall of the rectum rather than a closed semipermeable wall interposed in the rectum.

In FIG. 7, and accompanying FIGS. 8-10, the dialysis device of the invention is shown at 110 and comprises means 112 to circulate into and out of the body a first, circulating dialyzing fluid 102 of a selected composition typically to withdraw contaminants from the body fluids, but optionally to add e.g. medicaments to the body. Additional or withdrawl is effected by osmotic diffusion through the semipermeable membrane described. A typical usage is the withdrawl of the body fluid components such as uric acid which circulate in the bloodstream and perfuse into the body fluids at the surface of veins, arteries and other body parts, and particularly, in this embodiment at the blood rich inner wall of the rectum, from which they can be removed in accordance with the present invention.

In this embodiment the internal chamber 124 is a bag of semipermeable material 124a closely fitted to inside wall 121 of the rectum 123 such that dialysis is effected across the membrane throughout the effective length of the rectum. The rectum 123 is of course connected to the lower end 125 of the intestine 127, but communication is cut off by surgically built wall 129, body waste being diverted to a by-pass tube 131 for accumulation and eventual diaposal via valve 133 and collector 135. The arrangement is similar to that obtaining after a colostomy and frees the rectum for use as a dialysis site.

Within the chamber 124 a deflector 137 is provided, an inverted dome held by spider 139 on tubular stem 141, whereby fluid 102 passed under pressure into the stem is deflected downward within the rectum-encased internal chamber 124 and the fluid accumulates to a greater or lesser depth, and preferably to have the chamber 124 hydraulically fully.

The first dialysis fluid 102 with its burden of contaminants is passed from the rectum 123 at the anus 143 where outlet 118 is fitted to the chamber 124 at 145.

The fluid 102 circulating means 112 includes a first pump 108, a body inlet 114 of the dialysis fluid chamber. The circulating dialysis fluid 102 is pumped by pump 108 through the inlet 114 and into the internal chamber 124 where stem portion 141 of the inlet 114 is disposed within the rectum for deflection and recovery as just described. The used dialysis fluid 102 is passed along outlet 118 to the regeneration stage. In the present embodiment, the regeneration stage uses a belt arrangement as in previous embodiments but with some differences. The outlet 118 delivers the fluid 102 to be regenerated to tubing 126 disposed in a lower portion 122a of belt 122 which is filled with distilled water 101 whence uric acid and other salt contaminants may be deleted from the fluid 102, the water eventually being drawn off as previously described. The tubing 126 is then passed to an upper portion 122b of the belt 122 which is filled with second dialysis fluid 154. The recirculating fluid 102 may be passed multiple times around the belt 122 rather than the limited number shown, as needed.

The fluid 102 is passed to a metal filter cartridge 149 comprising sintered metal and charcoal for removal of metallic contaminants from the fluid. The advantage of using a dialysis fluid rather than blood as the circulating medium, as taught herein, is illustrated by being able to filter metallic contaminants from the fluid, as just described, a step not available when blood is the medium rather than "artificial blood" as the circulating fluid 102 may be called.

After regeneration and filtration as noted, the fluid 102 is pumped by pump 108 to inlet 114 and thence on to the rectum 123 as described above.

As in previous embodiments, the second dialysis fluid 154 may be of a composition like the first, varied to add to our subtract from the first dialysis fluid those materials needed for effective kidney function. The regeneration of the second dialysis fluid 154 may be effected as in earlier embodiments and will not be further described here, except to note the presence of filter-tank elements 136, 138 and 140 in FIG. 7 for the regeneration of fluid 154 passed therethrough by pump 134. The distilled water 101 may be readily replaced as necessary.

With reference now to FIG. 11, in which like parts to those in FIGS. 7-10 are given the same number, the rectum 123 is used per se as the internal chamber 124 without interposition of a semipermeable membrane wall such as wall 124a in FIG. 7. For this purpose, the rectum 123 is cut off from the intestine 127 and a by-pass for waste 124a in FIG. 7. For this purpose, the rectum 123 is cut off from the intestine 127 and a by-pass for waste 131 provided. The rectum 123 is ported at its upper end to receive incoming first dialysis fluid from inlet 114a which enters the body tissue at 115, and is closed at its lower end by the anal sphincter is sufficient or a plug arrangement which enables retention of the fluid in the rectum for dialysis. Outlet 118 leads from the anus to the regeneration stage described in connection with FIG. 7. The embodiment of FIG. 11 offers an optimum combination of blood-rich surface for dialysis, minimum foreign material insertion into the body, and the advantage of use of a natural cavity.

It is thus seen that an artificial kidney function can be both wearable and internal. The belt mounting of the regeneration stage, and the interior disposal of the dialysis function for concurrent operation provides unparalled convenience and comfort to the user. Mere batch operations even effected within the body do not approach the present invention for uniformity of treatment and absence of user highs and lows since the treatment is continuous with regeneration of one portion of a common dialysis fluid being accomplished as another portion of that common fluid is being dialyzed against body fluids, and without necessary invasion of arteries and veins. In addition the regeneration fluid is itself regenerated automatically as the dialysis fluid is renenerated, and all by wearable apparatus.

The present invention provides in a single integrated system many long sought characteristics of the ideal artificial kidney, including nonmedication of the blood, wearability, continuity of treatment, uniformity of treatment, non-invasive procedures, maximization of rate of dialysis consistent with internal effectuation, and ready removal of water and contaminants so that the user is a close to leading a normal existence as can be.

The foregoing objects of the invention are thus realized including provision of a novel dialysis system for humans, in which the dialyzing effectiveness of earlier systems is retained, but in which in addition the problems inherent in dialyzing blood outside the body are avoided, which are internally operable, in which dialysis is conducted within the body, "in vivo" and the dialyzing fluid regenerated outside the body so that the dialyzing fluid and not blood circulates to and from the body, and in which body fluids other than intravenous or intraarterial blood are used for purposes of dialysis against a dialyzing fluid, and in non-critical areas of the body, such as adjacent the intestines and within the peritoneal cavity, or the rectum, or advantageously with a section of the user's own tissue, removed and reconnected so as to be common living tissue with the intestine but to be out of fluid communication with the waste products.

I claim:

1. Wearable, continuously internally operable and externally regnerable dialysis device comprising means concurrently dialyzing a confined dialysis dluid against body fluids within the body intestines and regenerating said dialysis fluid outside the body.

2. Wearable, continuously internally operable and externally regenerable dialysis device according to claim 1, in which said means includes pump means for exchanging said dialysis fluid from within and outside the body.

3. Wearable, continuously internally operable and externally regenerable dialysis device according to to claim 1, in which said means includes an internal chamber disposed within the body for confining said dialysis fluid, said chamber having a semipermeable wall adapted to dialysis.

4. Wearable, continuously internally operable and externally regenerable dialysis device according to claim 1, in which said means includes an external chamber disposed outside the body, said external chamber having a semipermeable wall for dialyzing spent dialysis fluid there against a regenerating fluid.

5. Wearable, continuously internally operable and externally regenerable dialysis device according to claim 1, in which said means includes conduit means continuously communicating the confined portion of said dialysis fluid with dialysis fluid outside the body.

6. Wearable, continuously internally operable and externally regenerable dialysis device comprising a body fluid-dialyzing semipermeable generally tubular internal chamber resistant to deterioration from exposure within the body, and an external chamber, said internal chamber being adapted to extended disposition within a user's body intestines in body fluid-dialzying relation and freely of interior communication with veins and arteries, said external chamber being in continuous open communication with said internal chamber, a pump to exchange a first dialysis fluid between said internal chamber and said external chamber, and means to regenerate said first dialysis fluid during passage through said external chamber for return to said internal chamber.

7. Wearable, continuously internally operable and externally regenerable dialysis device according to claim 6, in which said internal chamber is elongated and located inward of the peritoneum, and including also a continued extent of said chamber defining a conduit for passing first dialysis fluid through said peritoneum.

8. Wearable, continuously internally operable and externally regenerable dialysis device according to claim 7, in which said internal chamber comprises a section of the large or small intestine out of interior fluid communication with the intestine from which it is take, but constituted of common living tissue therewith.

9. Wearable, continuously internally operable and externally regenerable dialysis device according to claim 8, in which said external chamber is an elongated tube adapted to contain said first dialysis fluid, and including also an envelope surrounding said tube for holding said second dialysis fluid against said tube in dialyzing relation to regenerate said first dialyzing fluid.

10. Wearable, continuously internally operable and externally regenerable dialysis device according to claim 9, in which said envelope comprises a second tube surrounding said external chamber tube along its length.

11. Wearable, continuously internally operable and externally regenerable dialysis device according to claim 9, including also valve means selectively openable to draw said second dialysis fluid from said envelope.

12. Wearable, continuously internally operable and externally regenerable dialysis device according to claim 9, in which said means to exchange said first dialysis fluid includes a first pump in open communication with said internal and external chambers.

13. Wearable, continuously internally operable and externally regenerable dialysis device according to claim 12, including also means to regenerate said first dialysis fluid by addition or subtraction of components for dialysis in said first dialysis fluid.

14. Wearable, continuously internally operable and externally regenerable dialysis device according to claim 13, including also a waist encircling belt carrying said envelope and supporting said external chamber therein, and belt-carried means supporting said first pump and regenerating means at the hip region of the wearer.

15. Wearable, continuously internally operable and externally regenerable dialysis device according to claim 14, in which said external chamber is disposed within said belt in multiply reverse-turned relation, and including also a second pump for circulating said second dialysis fluid through said envelope.

16. Wearable, continuously internally operable and externally regenerable dialysis device according to claim 12, in which said means to exchange said first dialysis fluid includes a first pump in open communication with said chambers.

17. Wearable, continuously internally operable and externally regenerable dialysis device according to claim 16, including also a second pump in open communication with said envelope, a solids adjustment zone in open communication with envelope comprising means selected from a filter means and a supply of second dialysis fluid make-up solids in flow communication with said zone for adding to or removing solids from said second dialysis fluid pumped by said pump.

18. Wearable, continuously internally operable and externally regenerable dialysis device according to claim 17 in which said first and second pumps are external of the body.

19. Wearable, continuously internally operable and externally regenerable dialysis device comprising a body fluid dialyzing internal chamber sized and arranged to define an extended dialyzing interface with body fluids outside the veins and arteries of the user's body, said internal chamber being integral with living tissue of the user's intestine, and free of interior open communication with said intestine.

20. Wearable, continuously internally operable and externally regenerable dialysis device comprising a body fluid dialyzing internal chamber sized and arranged to define an extended dialzying interface with body fluids outside the veins and arteries of the user's body, said internal chamber being defined by the living tissue of the user's body, said internal chamber being defined by the living tissue of the user's rectum, and free of interior open communication with the user's intestine.

21. Wearable, continuously internally operable and externally regenerable dialysis device comprising a body fluid dialyzing internal chamber sized and arranged to define an extended dialzying interface with body fluids outside the veins and arteries of the user's body, said internal chamber being defined by a closed semipermeable wall disposed within the user's rectum free of interior open communication with the user's intestine.

22. Wearable, continuously internally operable and externally regenerable dialysis device according to claim 19, 20 or 21, including also means to exchange said first dialysis fluid from within the body into and through said external chamber for regeneration against a second dialysis fluid of different composition for adding or subtracting components form said circulating dialysis fluid according to the user's need.

23. Wearable, continuously internally operable and externally regenerable dialysis device comprising a body fluid-dialzying internal chamber an external chamber in continuous open communication therewith, said internal chamber being defined at least in part by the rectum out of communication with the intestine and adapted to contain dialyzing fluid in body fluid-dialyzing relation, pump means to exchange a first dialysis fluid between said internal and external chambers and means to dialyze said first dialysis fluid in said external chamber for return to said internal portion and concurrently with said exchange.

24. Wearable, continuously internally operable and externally regenerable dialysis device according to claim 23, including also said external chamber being an elongated tube, an envelope surrounding said tube, and a second dialyzing fluid within said envelope for regenerating said circulating dialysis fluid within said external chamber.

25. Wearable, continuously internally operable and externally regenerable dialysis device according to claim 24, including also valve-controlled means to tap said second dialysis fluid from said envelope.

26. Wearable, continuously internally operable and externally regenerable dialysis device for a person having a by-passed rectum as by a colostomy, said device having an internal chamber and an external chamber, said internal chamber being defined by the rectum of the wearer, whereby fluids passed from the rectum interior wall, said external chamber comprising a body fluid-dialyzing relation with the rectum interior wall, said external chamber comprising a body fluid-dialyzing semipermeable chamber in open communication with said internal chamber, means to exchange dialysis fluid between said internal and external chambers, and means to regenerate said first dialysis fluid within said external chamber for return to said internal chamber for continuing body fluid dialysis.

27. Wearable, continuously internally operable and externally regenerable dialysis device according to claim 26, including also a deflector adapted to deflect dialysis fluid within the rectum into dialyzing proximity with the rectum interior wall.

28. Wearable, continuously internally operable and externally regenerable dialysis device according to claim 26, including also a closed semipremeable wall disposed within the rectum for confining said first dialysis fluid within the rectum.

29. Wearable, continuously internally operable and externally regenerable dialysis device according to claim 27 or 28, in which said means to exchange dialysis fluid further includes means defining a first fluid passage to the rectum, and means defining a second fluid passage out of the rectum via the anus.

30. Wearable, continuously internally operable and externally regenerable dialysis device according to claim 28, in which said external chamber is an elongated tube adapted to contain said first dialysis fluid, and including also an envelope surrounding said tube for holding said second dialysis fluid against said tube in dialyzing relation to regenerate said first dialyzing fluid.

31. Wearable, continuously internally operable and externally regenerable dialysis device according to claim 30, in which said envelope comprises a second tube surrounding said external chamber tube along its length.

32. Wearable, continuously internally operable and externally regenerable dialysis device according to claim 31, including also valve means selectively openable to draw an aliquot portion of said second dialysis fluid from said envelope.

33. Wearable, continuously internally operable and externally regenerable dialysis device according to claim 32, in which said means to exchange said first dialysis fluid includes a first pump in open communication with said chambers.

34. Wearable, continuously internally operable and externally regenerable dialysis device according to claim 33, including also means to regenerate said second dialysis fluid by addition or subtraction of components for dialysis of said first dialysis fluid.

35. Wearable, continuously internally operable and externally regenerable dialysis device according to claim 34, in which said pump and regenerating means are body-external.

36. Wearable, continuously internally operable and externally regenerable dialysis device according to claim 35, including also a waist encircling belt carrying said envelope and supporting said external chamber therein, and belt-carried means supporting said pump and regenerating means at the hip region of the wearer.

37. Wearable, continuously internally operable and externally regenerable dialysis device according to claim 36, in which said body-external portion is disposed within said belt in multiply reverse-turned relation.

38. Method for the continuous dialyzing of body fluid within the body, including urging a first dialysis fluid through the body intestines in body-fluid dialyzing relation and dialyzing said first dialysis against a second dialysis fluid differing in composition from said first dialysis fluid in first dialyzing fluid regenerating relation.

39. The method according to claim 38 including also disposing an internal chamber within and an external chamber without the user's body freely of interior communication with veins and arteries of the body for exchange of said first dialysis fluid between said chambers, said external chamber comprising a semipermeable membrane, said internal chamber being in dialyzing communication with body fluids within the body, and said external chamber being in dialzying communication with said second dialysis fluid outside the body.

40. The method according to claim 39, including also employing a tissue of the user's body to define the internal chamber in dialyzing communication with body fluids.

41. The method according to claim 40, including also selecting a section of the user's intestine and connection said section be be common living tissue with said intestine but out of interior fluid communication therewith to define the internal chamber in dialyzing communication with body fluids.

42. The method according to claim 40, including also selecting a section of the user's rectum isolated from the intestine to define the internal chamber, introducing said first dialyzing fluid thereinto and withdrawing said fluid at the anal opening, said fluid being diffused in dialzying contact with the rectum wall between said introduction and withdrawl.

43. The method according to claim 42, including also interposing a semipermeable wall between said first dialysis fluid and said rectum wall, whereby said semipermeable wall dialyzes body fluids within the rectum wall against said first dialysis fluid.

44. Method for dialysis including concurrently dialyzing a confined dialysis fluid against body fluids within the body intestines and regnerating said dialysis fluid outside the body.

45. The method according to claim 44, including also exchanging said dialysis fluid outside the body for dialysis fluid within the body to renew the dialysis fluid within the body.

46. The method according to claim 44, including also employing a section of the user's body tissue to confine said dialysis fluid within the body.

47. The method according to claim 46, including also employing a semipermeable membrane to confine said dialysis fluid within the body.

48. The method according to claim 44, including also dialyzing spent dialysis fluid from within the body against a regenerating fluid outside the body.

49. The method according to claim 48, including also continuously exchanging the confined portion of said dialysis fluid with said dialysis fluid outside the body.

50. Method for internally dialyzing the body while externally regenerating the dialysis fluid including confining within the body intestines a common dialyzing fluid in body fluid dialyzing relation, regenerating said common dialysis fluid against a second dialysis fluid outside the body, and exchanging said regenerated dialysis fluid with said confined dialysis fluid.

51. The method according to claim 50, including also confining said common dialysis fluid within living tissue of the user.

52. The method according to claim 50, including also confining said common dialysis fluid within a semipermeable membrane.

53. The method according to claim 52, including also dialzying said semipermeable membrane confined fluid against the rectum wall of the user.

* * * * *